US010583001B2

(12) United States Patent
Navia et al.

(10) Patent No.: US 10,583,001 B2
(45) Date of Patent: Mar. 10, 2020

(54) METHODS FOR REPLACING A CARDIAC VALVE (71) Applicant: The Cleveland Clinic Foundation, Cleveland, OH (US)

(72) Inventors: Jose L. Navia, Shaker Heights, OH (US); Jose A. Navia, Buenos Aires (AR); Carlos Oberti, Westlake, OH (US)

(73) Assignee: THE CLEVELAND CLINIC FOUNDATION, Cleveland, OH (US)

( * ) Notice: Subject to any disclaimer, the term of this patent is extended or adjusted under 35 U.S.C. 154(b) by 0 days.

(21) Appl. No.: 14/048,987

(22) Filed: Oct. 8, 2013

(65) Prior Publication Data
US 2014/0039613 A1 Feb. 6, 2014

Related U.S. Application Data (62) Division of application No. 11/357,485, filed on Feb. 18, 2006, now abandoned.

(60) Provisional application No. 60/654,725, filed on Feb. 18, 2005.

(51) Int. Cl.
*A61F 2/24* (2006.01)
*A61F 2/848* (2013.01)

(52) U.S. Cl.
CPC .......... *A61F 2/2412* (2013.01); *A61F 2/2409* (2013.01); *A61F 2/2418* (2013.01); *A61F 2/2445* (2013.01); *A61F 2/2457* (2013.01); *A61F 2002/8483* (2013.01); *A61F 2220/0016* (2013.01); *A61F 2220/0075* (2013.01); *A61F 2230/0013* (2013.01)

(58) Field of Classification Search
CPC ........ A61F 2/24; A61F 2/2409; A61F 2/2418; A61F 2/2412; A61F 2/2439
See application file for complete search history.

(56) References Cited

U.S. PATENT DOCUMENTS

| 6,425,916 B1* | 7/2002 | Garrison et al. ............. 623/2.11 |
| 2001/0007956 A1* | 7/2001 | Letac .................... A61F 2/2412 623/2.11 |
| 2004/0210304 A1* | 10/2004 | Seguin et al. ............... 623/2.11 |
| 2005/0137688 A1* | 6/2005 | Salahieh ............... A61F 2/2418 623/2.11 |

* cited by examiner

Primary Examiner — Leslie Lopez
(74) Attorney, Agent, or Firm — Kurt T. Mulvilie; VLP Law Group, LLP (57) ABSTRACT A method for replacing a cardiac valve includes an expandable support member having oppositely disposed first and second ends, a main body portion extending between the ends, and a prosthetic valve within the main body portion. The main body portion has an annular shape for expanding into position in the annulus of the valve. The first and second ends include a plurality of upper and lower wing members movable from a collapsed condition into an extended condition for respectively engaging a first section of cardiac tissue surrounding the valve and for: engaging a portion of the native valve leaflets to pin the leaflets back against the annulus. The second end further includes at least two strut members spaced apart from each other. A respective one of the strut members is attached to at least one commissural section of the prosthetic valve to prevent prolapse of the valve leaflets.

12 Claims, 8 Drawing Sheets

METHODS FOR REPLACING A CARDIAC VALVE

RELATED APPLICATION

This application is a divisional of application Ser. No. 11/357,485 filed Feb. 18, 2006, which claims priority from U.S. provisional patent application Ser. No. 60/654,725, filed on Feb. 18, 2005, the subject matter of which is incorporated herein by reference.

FIELD OF THE INVENTION

The present invention relates to an apparatus and methods for treating a diseased cardiac valve, and is particularly directed to an apparatus and methods for the correction of mitral valve and tricuspid valve disorders via a minimally invasive or percutaneous approach.

BACKGROUND OF THE INVENTION

There are two atrio-ventricular valves in the heart; one on the left side of the heart and one on the right side of the heart. The left side atrio-ventricular valve is the mitral valve and the right side atrio-ventricular.

The mitral and tricuspid valves differ significantly in anatomy. While the annulus of the mitral valve is generally D-shaped, the annulus of the tricuspid valve is more circular. The effects of the valvular dysfunction vary between the mitral valve and the tricuspid valve. Mitral valve regurgitation has more severe physiological consequences to the patient than does tricuspid valve regurgitation, a small amount of which is tolerable.

In mitral valve insufficiency, the valve leaflets do not fully close and a certain amount of blood leaks back into the left atrium when the left ventricle contracts. As a result, the heart has to work harder by pumping not only the regular volume of the blood, but also the extra volume of blood that regurgitated back into the left atrium. The added workload creates an undue strain on the left ventricle. This strain can eventually wear out of the heart and result in morbidity when the conditions are prolonged and severe enough. Consequently, proper function of the mitral valve is critical to the pumping efficiency of the heart.

Mitral and tricuspid valve disease is traditionally treated by either surgical repair with an annuloplasty ring or surgical replacement with a valve prosthesis. However, surgical valve replacement or repair is often an exacting operation that is done through a surgical technique where the thoracic cavity is opened. The operation requires use of a heart-lung machine for external circulation of the blood as the heart is stopped and opened during the surgical intervention and the artificial cardiac valves and/or annuloplasty rings are sewed in under direct vision. This operation exposes the patient to many risks especially in the elderly population. A percutaneous procedure that can be performed under local anesthesia in the cardiac catherization lab, rather than in cardiac surgery, could therefore offer tremendous benefits for these patients, many of whom have no options today. Consequently, an apparatus for replacing a diseased atrioventricular valve using a minimally invasive, percutaneous approach would be very helpful to provide additional opportunities to treat patients with severe valvular insufficiency, end stage heart failure, atrial fibrillation, and/or other associated arrhythmias.

SUMMARY OF THE INVENTION

In one aspect of the present invention, an apparatus for replacing a cardiac valve having at least two native valve leaflets is provided. The apparatus comprises an expandable support member having oppositely disposed first and second ends and a main body portion extending between the ends. The main body portion of the support member has an annular shape for expanding into position in the annulus of the cardiac valve. The first end comprises a plurality of upper wing members that extend from the main body portion. Each of the upper wing members is movable from a radially collapsed condition into a radially extended condition for engaging a first section of cardiac tissue surrounding one side of the cardiac valve. The second end comprises a plurality of lower wing members that extend from the main body portion. Each of the lower wing members is movable from a radially collapsed condition into a radially extended condition for engaging a portion of the native valve leaflets to pin the leaflets back against the annulus of the native cardiac valve. The second end of the support member further includes at least two strut members that are spaced apart from each other. The at least two valve leaflets are joined at at least two commissural sections that are spaced apart from each other. Each of the at least two commissural sections are attached to a respective one of the strut members to prevent prolapse of the valve leaflets. A prosthetic valve is secured within the main body portion of the support member. The prosthetic valve has at least two valve leaflets that are coaptable to permit unidirectional flow of blood.

In another aspect of the present invention, at least a portion of the support member is treated with at least one therapeutic agent for eluting into cardiac tissue.

In yet another aspect of the present invention, a method for replacing a cardiac valve having at least two native valve leaflets is provided. According to the inventive method, a prosthetic valve having at least two valve leaflets that are coaptable to permit unidirectional flow of blood is provided. The prosthetic valve includes an expandable support member having oppositely disposed first and second ends and a main body portion extending between the ends. The expandable support member further includes a plurality of upper wing members that extend from one end of the main body portion, and a plurality of lower wing members that extend from an opposite end of the main body portion. The second end of the support member further includes at least two strut members. The prosthetic valve includes at least two valve leaflets that are joined together at at least two commissural sections. Each of the at least two commissural sections are attached to a respective one of the strut members to prevent prolapse of the valve leaflets. The main body portion of the prosthetic valve is placed within the annulus of the cardiac valve to be replaced, and is then expanded into engagement with the annulus of the cardiac valve to secure the prosthetic valve in the annulus. The upper wing members are deployed from a radially collapsed condition into a radially extended condition into engagement with a first section of cardiac tissue surrounding one side of the cardiac valve. The lower wing members are deployed from a radially collapsed condition into a radially extended condition into engagement with a portion of the native valve leaflets to pin the leaflets back against the annulus of the native cardiac valve.

BRIEF DESCRIPTION OF THE DRAWINGS

The foregoing and other features of the present invention will become apparent to those skilled in the art to which the present invention relates upon reading the following description with reference to the accompanying drawings, in which.

DETAILED DESCRIPTION OF EMBODIMENTS

Figure 1:
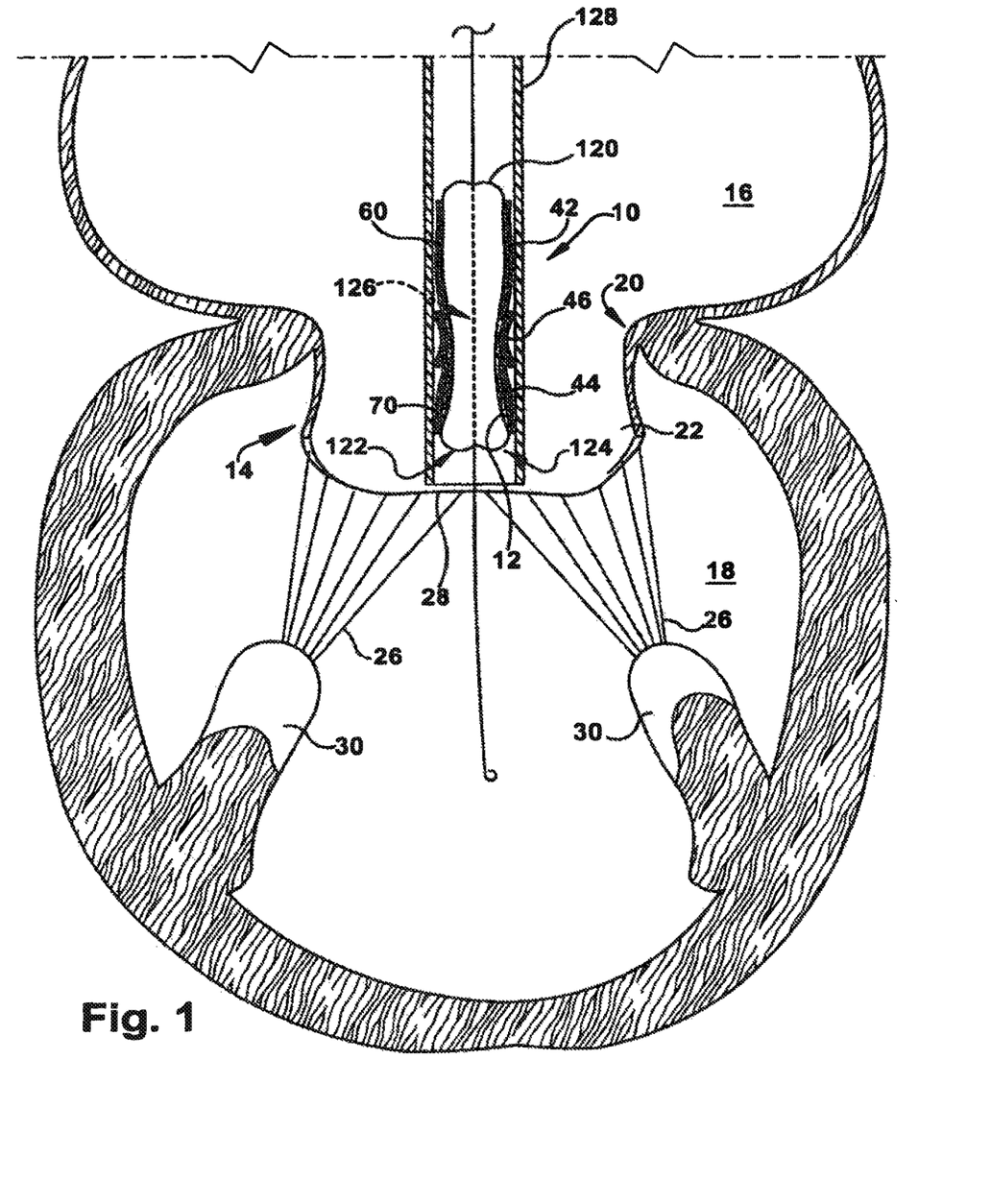
FIG. 1 is a schematic sectional view of an apparatus for replacing a diseased cardiac valve in accordance with the present invention and illustrating the apparatus being delivered to the diseased valve in a collapsed condition through a percutaneous procedure.
Figure 2:
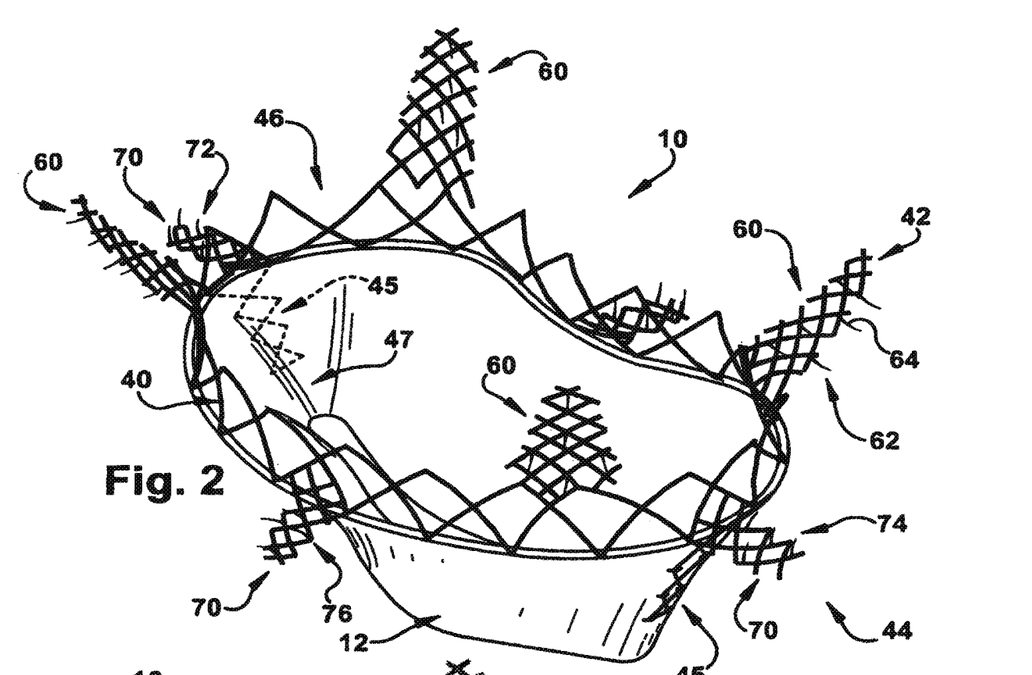
FIG. 2 is a perspective view of the apparatus of FIG. 1 in a radially expanded condition.

The present invention relates to an apparatus and methods for treating a diseased cardiac valve, and is particularly directed to an apparatus and methods for the correction of mitral valve and tricuspid valve disorders via a minimally invasive and/or percutaneous approach. As representative of the present invention, FIGS. 1 and 2 illustrate an apparatus 10 that includes a prosthetic valve 12 for replacing a dysfunctional cardiac valve, such as a mitral valve 14, by inserting the prosthetic valve over the native mitral valve so that the prosthetic valve assumes the valvular function. It should be understood, however, that the apparatus 10 disclosed herein could also be used to replace other cardiac valves, such as a tricuspid, pulmonary, or aortic valve.

Figure 6:
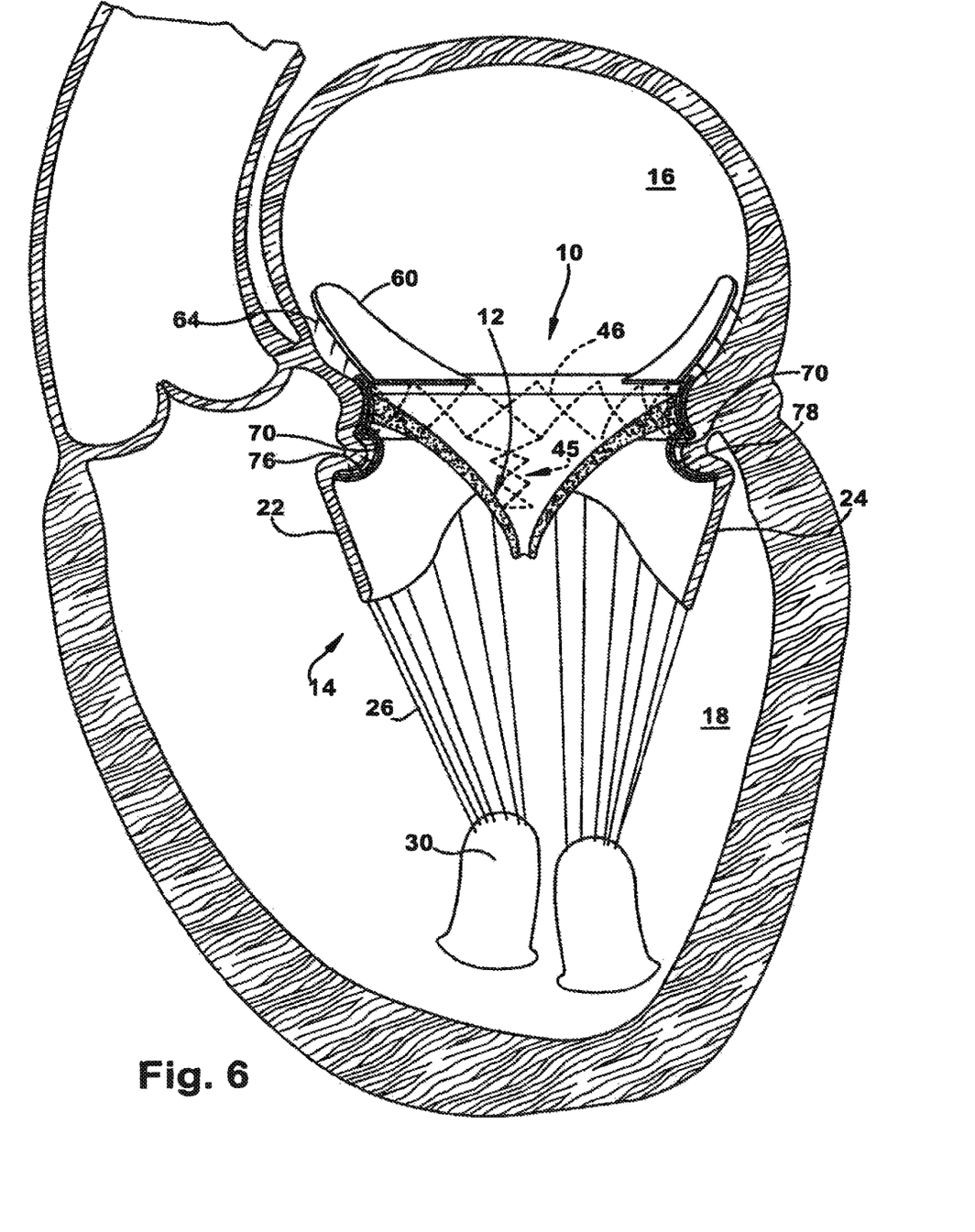
FIG. 6 is a schematic sectional view taken along 6-6 in FIG. 5.
Figure 7:
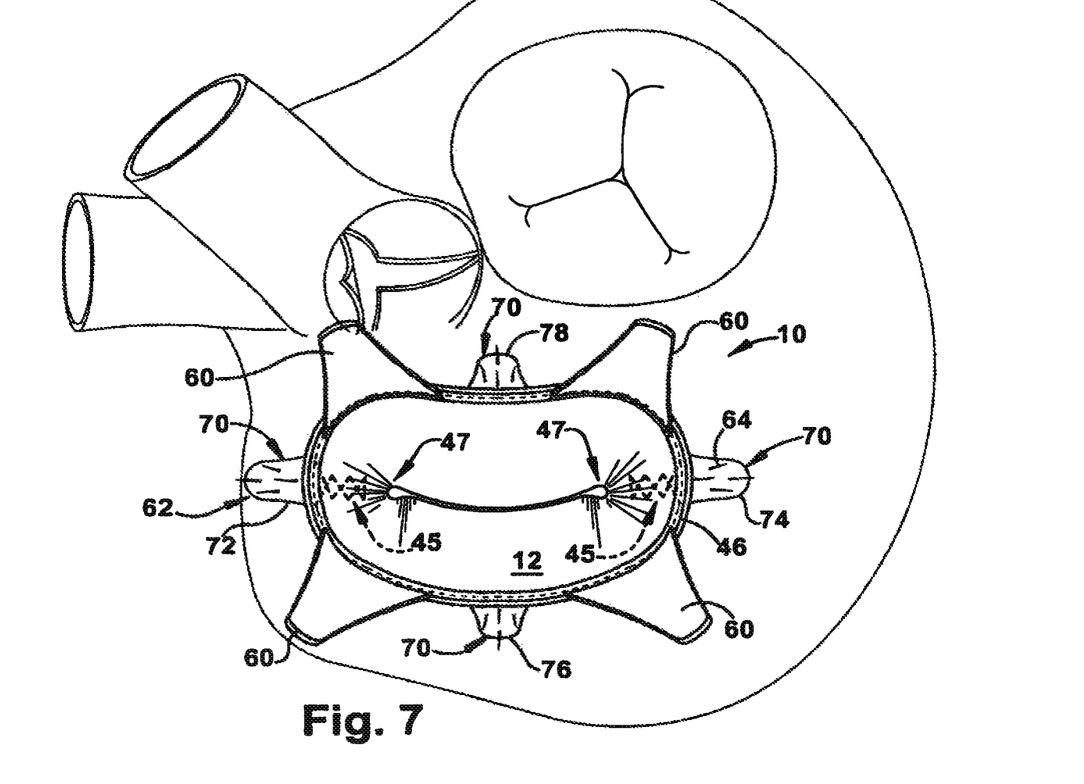
FIG. 7 is a schematic top view taken along line 7-7 in FIG. 5 with parts omitted for clarity.
Figure 8:
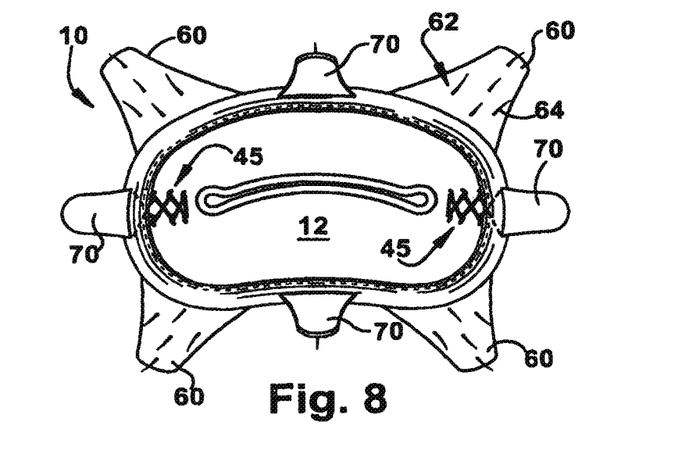
FIG. 8 is a schematic bottom view taken along line 8-8 in FIG. 5 with parts omitted for clarity.

As shown in FIG. 1, the mitral valve 14 is located between the left atrium 16 and the left ventricle 18 and functions to prevent the backflow of blood from the left ventricle into the left atrium during contraction. The mitral valve 14 has a D-shaped annulus 20 that defines the opening between the left atrium 16 and the left ventricle 18. The mitral valve 14 is formed by two leaflets; namely, the anterior leaflet 22 and the posterior leaflet 24 (FIG. 6). The anterior leaflet 22 extends along the generally planar base of the D-shaped valve annulus 20, while the posterior leaflet 24 extends arcuately around the curved portion of the D-shaped annulus of the mitral valve 14. Chordae tendinea 26 (FIG. 1) extend between the free edges 28 of both leaflets 22 and 24 to the papillary muscles 30 in the left ventricle 18.

The apparatus 10 for replacing the dysfunctional mitral valve 14 includes an expandable support member 40 (FIG. 2), commonly referred to as a stent, and the prosthetic valve 12. The support member 40 has a known stent configuration that allows it to be collapsed and expanded. The support member 40 may be made from any suitable medical grade metal or plastic, including shape memory materials such as Nitinol, stainless steel, and/or titanium.

The support member 40 is annular in shape and includes oppositely disposed first and second ends 42 and 44 with a main body portion 46 extending between the ends. As shown in FIGS. 2-8, when the support member 40 is expanded, the main body portion 46 has a concave cross-sectional shape for conforming to the convex shape of the valve annulus 20.

Figure 3:
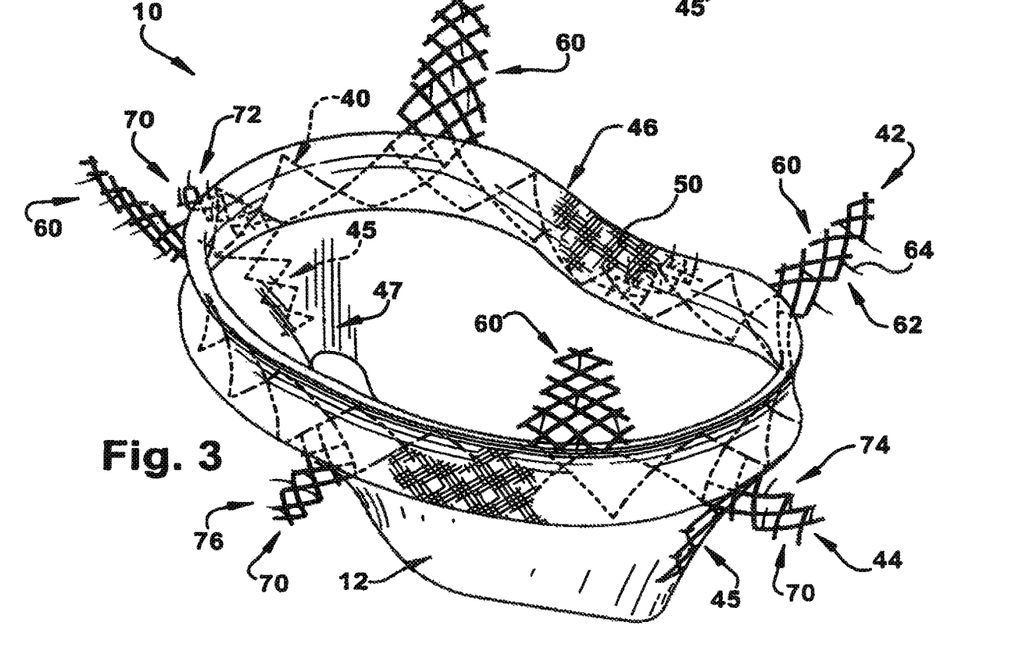
FIG. 3 is a perspective view showing an alternative embodiment of the apparatus in FIG. 2.
Figure 4:
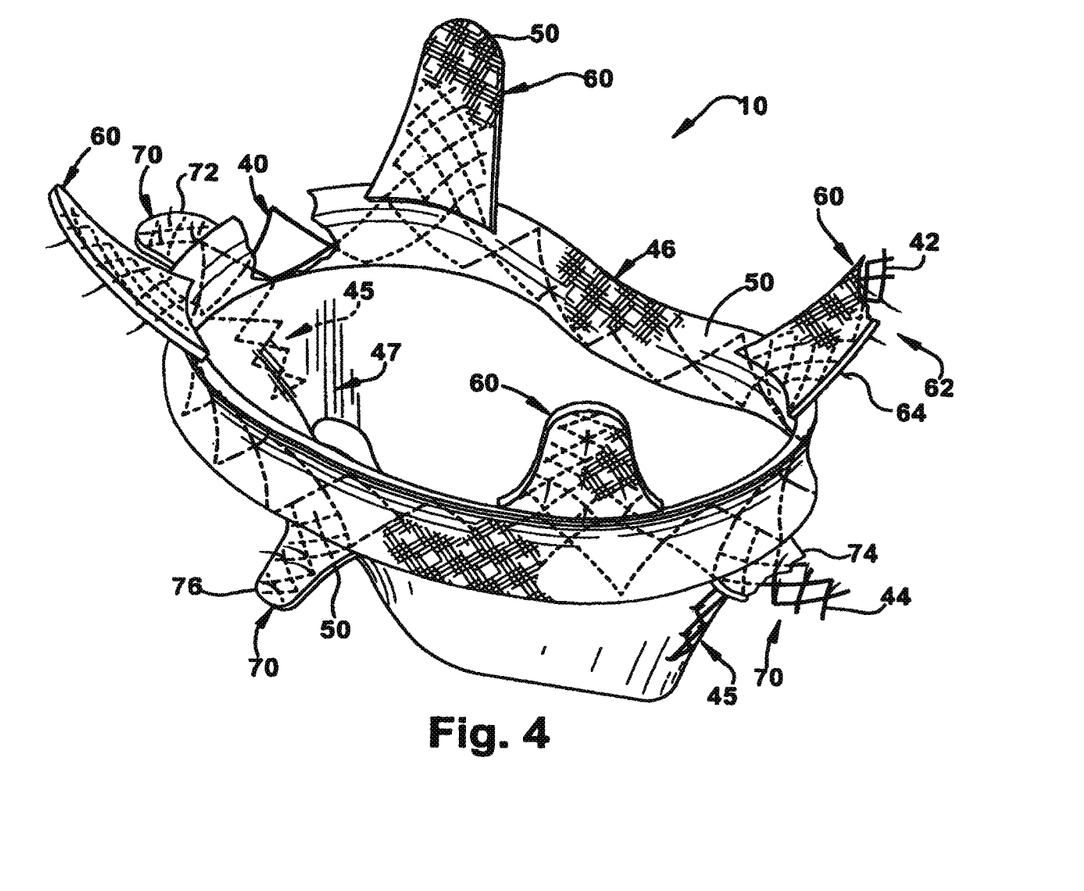
FIG. 4 is a perspective view showing another alternative embodiment of the apparatus shown in FIG. 2.

The apparatus 10 may further include a layer 50 (FIG. 3) of biocompatible material covering at least a portion of the support member 40. The layer 50 of biocompatible material may be a synthetic such as Dacron® (Invista, Wichita, Kans.), Gore-Tex® (W. L. Gore & Associates, Flagstaff, Ariz.), woven velour, polyurethane, polytetrafluoroethylene (PTFE), or heparin-coated fabric. Alternatively, the layer 50 may be a biological material such as bovine or equine pericardium, peritoneal tissue, an allograft, a homograft, patient graft, or a cell-seeded tissue. The layer 50 can cover either the inside surface of the support member 40, the outside surface of the support member, or can be wrapped around both the inside and outside surfaces. The layer 50 may be attached around the entire circumference of the support member 40 or, alternatively, may be attached in pieces or interrupted sections to allow the support member to more easily expand and contract. As shown in FIG. 3, for example, only the main body portion 46 of the prosthetic valve 12 may be covered with the layer 50 of biocompatible material. Alternatively, the support member 40 may be entirely covered with the layer 50 of biocompatible material (FIG. 4).

The first end 42 of the support member 40 comprises a plurality of upper wing members 60 that extend integrally from the main body portion 46. In the embodiment illustrated in FIGS. 1-8, there are four upper wing members 60 spaced about the circumference of the support member 40, but it should be understood that more or less than four upper wing members could be used. The upper wing members 60 are movable from the radially collapsed condition of FIG. 1 to the radially extended condition of FIGS. 2-8. Each upper wing member 60 may also include at least one attachment mechanism 62, such as a barb 64 or suture, for embedding into a first section of cardiac tissue (e.g., the wall of the left atrium 16) to help secure the support member 40 in the annulus 20 of the mitral valve 14.

The second end 44 of the support member 40 comprises a plurality of lower wing members 70 that extend integrally from the main body portion 46. In the embodiment illustrated in FIGS. 1-8, there are four lower wing members 70 spaced about the circumference of the support member 40. More specifically, there are first and second lower wing members 72 and 74, spaced approximately 180° apart, for positioning at the commissures of the native mitral valve 14, and third and fourth lower wing members 76 and 78 (FIG. 7), spaced approximately 180° apart, for positioning directly over respective central portions of the native leaflets 22 and 24. The third and fourth lower wing members 76 and 78 are spaced in-between the first and second lower wing members 72 and 74, respectively. It is contemplated, however, that more or less than four lower wing members 70 could be used. Further, it is contemplated that the third and fourth lower wing members 76 and 78 positioned over the leaflets 22 and 24 could be omitted completely.

Each of the lower wing members 70 is movable from the radially collapsed condition of FIG. 1 to the radially extended condition of FIGS. 2-8 for engaging a portion of the native valve leaflets 22 and 24 to pin the leaflets back against the native valve annulus 20. The lower wing members 70 may also include at least one attachment mechanism 62, such as a barb 64 or suture, for embedding into at least one of the native valve leaflets 22 and 24 to help secure the support member 40 in the annulus 20 of the mitral valve 14.

The second end 44 of the support member 40 additionally includes at least two strut members 45. As shown in FIG. 2, the valve leaflets of the prosthetic valve 12 are joined together at at least two commissural sections 47 that are spaced apart from each other. Each of the at least two commissural sections 47 are attached to a representative one of the strut members 45 to prevent prolapse of prosthetic valve leaflets 90 and 92, described in detail below. The strut members 45 are securely attached to, and extend in a generally axial manner from, the support member 40. The strut members 45 are securely connected to the prosthetic valve 12 by sutures, for example, and may be made from any suitable medical grade metal or plastic, including shape memory materials such as Nitinol, stainless steel, and/or titanium. As illustrated in FIG. 2, the strut members 45 have a bare metal configuration and do not extend beyond the length of the prosthetic valve 12. It is contemplated, however, that the configuration of the strut members 45 may be varied as needed. For example, the strut members 45 may be covered by a layer 50 of biocompatible material and extend beyond the length of the prosthetic valve 12.

The prosthetic valve 12 of the present invention may comprise a stentless prosthetic valve. By "stentless" it is meant that the valve components including the leaflets of the prosthetic valve 12 are not reinforced with a support structure, such as a stent or other similar structure. The prosthetic valve 12 is secured, for example, by sutures or other suitable means within the main body portion 46 of the support member 40.

The prosthetic valve 12 may be fixed and preserved using a variety of known methods. The use of chemical processes for the fixation and preservation of biological tissues have been described and are readily available in the art. For example, glutaraldehyde, and other related aldehydes have seen widespread use in preparing cross-linked biological tissues.

Glutaraldehyde is a five carbon aliphatic molecule with an aldehyde at each end of the chain, rendering it bifunctional. These aldehyde groups react under physiological conditions with primary amine groups on collagen molecules resulting in the cross-linking of collagen containing tissues. Methods for glutaraldehyde fixation of biological tissues have been extensively described and are well known in the art. In general, a tissue sample to be cross-linked is simply contacted with a glutaraldeyde solution for a duration effective to cause the desired degree of cross-linking within the biological tissue being treated.

Many variations and conditions have been applied to optimize glutaraldehyde fixation procedures. For example, lower concentrations have been found to be better in bulk tissue cross-linking compared to higher concentrations. It has been proposed that higher concentrations of glutaraldehyde may promote rapid surface cross-linking of the tissue, generating a barrier that impedes or prevents the further diffusion of glutaraldehdye into the tissue bulk. For most bioprosthesis applications, the tissue is treated with a relatively low concentration glutaraldehyde solution, e.g., typically between 0.1%-5%, for 24 hours or more to ensure optimum fixation. Various other combinations of glutaraldehyde concentrations and treatment times will also be suitable depending on the objectives for a given application. Examples of such other combinations include, but are not limited to, U.S. Pat. Nos. 6,547,827, 6,561,970, and 6,878,168, all of which are hereby incorporated by reference in their entirety.

In addition to bifunctional aldehydes, many other chemical fixation procedures have been described. For example, some such methods have employed polyethers, polyepoxy compounds, diisocyanates, and azides. These and other approaches available to the skilled individual in the art for treating biological tissues are suitable for cross-linking vascular graft tissue according to the present invention.

The prosthetic valve 12 may also be treated and preserved with a dry tissue valve procedure as described in U.S. Pat. No. 6,534,004, the entire contents of which are hereby incorporated by reference. Furthermore, the prosthetic valve 12 may be treated with anti-calcification solutions, such as XenoLogiX® treatment (Edwards Lifesciences, Irvine, Calif.) or the SynerGraft® (CryoLife, Inc., Kennesaw, Ga.) treatment process, and/or anti-calcification agents, such as alfa-amino oleic acid.

Figure 9:
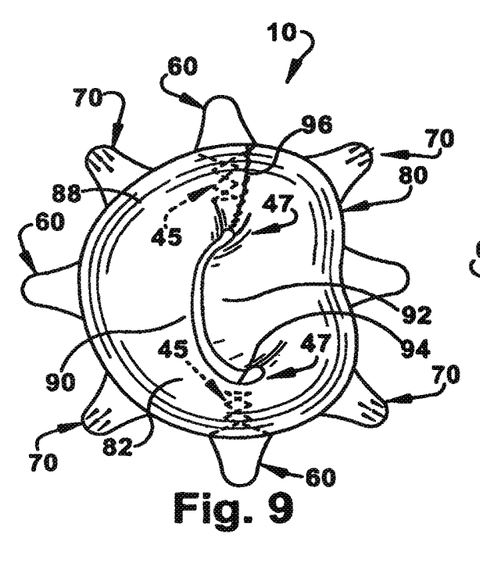
FIG. 9 is a plan view of the apparatus in FIG. 4 illustrating an alternative embodiment of the apparatus.
Figure 10:
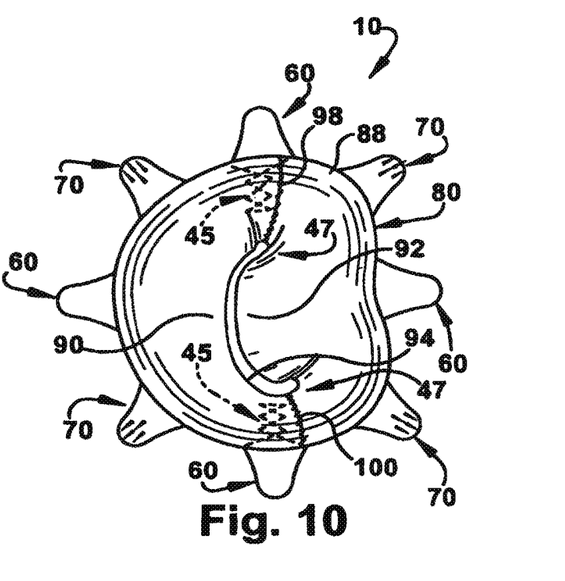
FIG. 10 is a view similar to FIG. 9 illustrating another alternative construction of the apparatus.

The prosthetic valve 12 can be made with only one piece of pericardial tissue, for example, as shown in FIG. 9. Where a single piece of pericardial tissue is used, a seam 96 is formed by suturing the ends of the tissue. Alternatively, the prosthetic valve 12 can be made with two pieces of pericardial tissue, one of which will form the first leaflet 90 and the other forms the second leaflet 92 of the prosthetic valve, as may be seen in FIG. 10. Where two pieces of pericardial tissue are used (FIG. 10), it is necessary to suture the tissue in two locations, thereby forming two seams 98 and 100. The seams 96, 98, and 100 are always placed at what will be the commissures of the prosthetic valve 12, where the first leaflet 90 meets the second leaflet 92.

Figure 11:
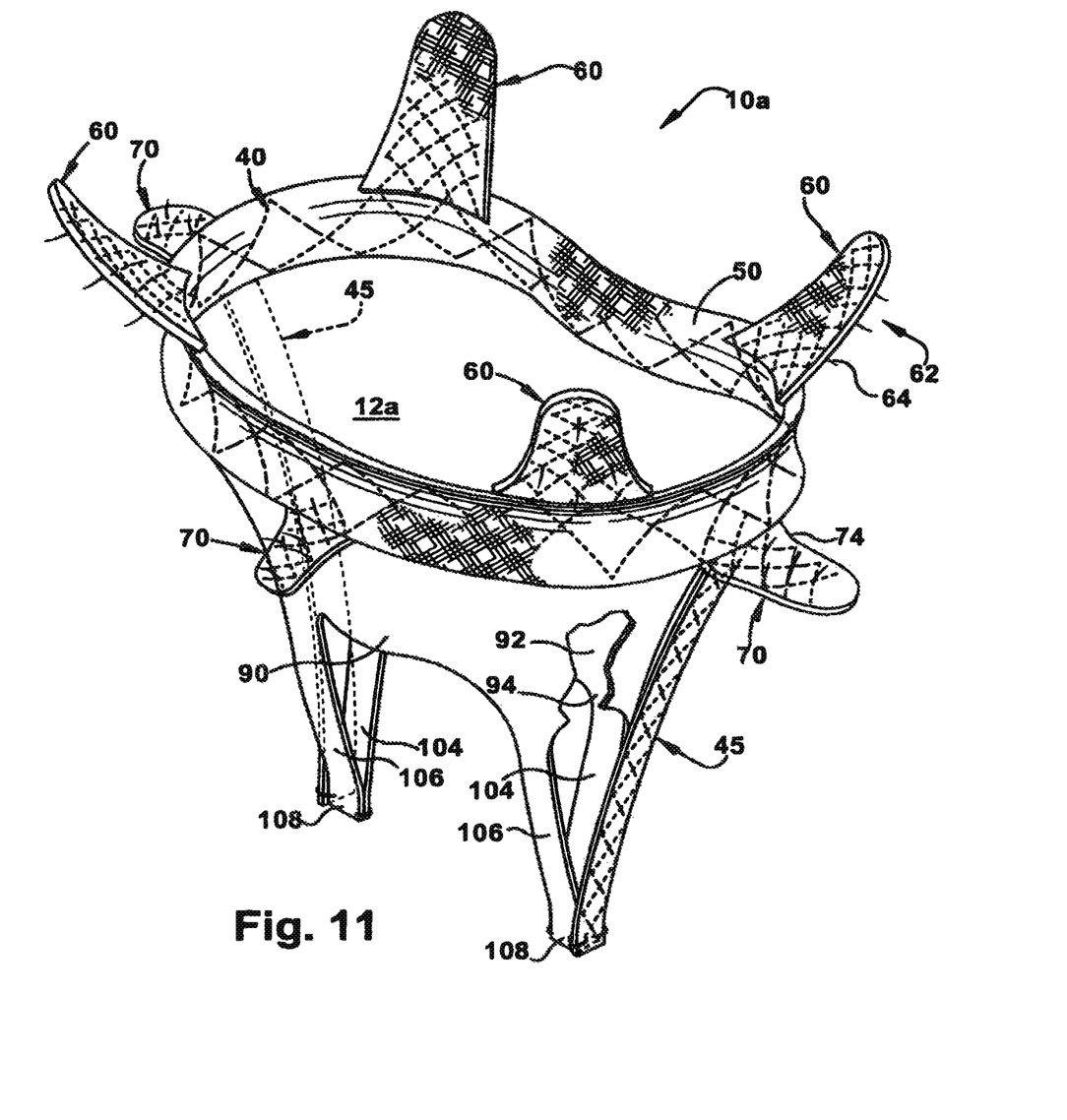
FIG. 11 is a perspective view showing an alternative embodiment of the apparatus in FIG. 4 having artificial chordae.

FIG. 11 illustrates an alternative embodiment of the present invention. The apparatus $10_a$ of FIG. 11 is identically constructed as the apparatus 10 of FIGS. 2-8, except whereas described below. In FIG. 11, structures that are identical as structures in FIGS. 2-8 use the same reference numbers, whereas structures that are similar but not identical carry the suffix "a".

As shown in FIG. 11, the apparatus $10_a$ includes an expandable support member 40 having a flexible configuration and a prosthetic valve $12_a$. The support member 40 is annular in shape and includes oppositely disposed first and second ends 42 and 44 with a main body portion 40 extending between the ends. The apparatus $10_a$ may further include a layer 50 of biocompatible material covering at least a portion of the support member 40.

The first and second ends 42 and 44 of the support member 40 respectively comprises a plurality of upper and lower wing members 60 and 70 that extend integrally from the main body portion 46. The upper and lower wing members 60 and 70 are movable from the radially collapsed condition of FIG. 1 to the radially extended condition of FIG. 11. Each upper wing member 60 may also include at least one attachment mechanism 62, such as a barb 64 or suture, for embedding into a first section of cardiac tissue (e.g., the wall of the left atrium 16) to help secure the support member 40 in the annulus 20 of the mitral valve 14. The lower wing members 70 may also include at least one attachment mechanism 62, such as a barb 64 or suture, for embedding into at least one of the native valve leaflets 22 and 24 to help secure the support member 40 in the annulus 20 of the mitral valve 14.

The prosthetic valve $12_a$ of the apparatus $10_a$ (and also the previously described valve 12) may comprise a stentless prosthetic valve, for example, having dimensions that correspond to the dimensions of the native mitral valve 14. Where the prosthetic valve $12_a$ is comprised of biological material, the biological material can include a harvested biological material such as bovine pericardial tissue, equine pericardial tissue, porcine pericardial tissue, animal or human peritoneal tissue, or mitral, aortic, and pulmonary xenograft or homograft. The biocompatible material may also include a suitable synthetic material such as polyurethane, expanded PTFE, woven velour, Dacron®, heparin-coated fabric, or Gore-Tex®.

The prosthetic valve $12_a$ further includes first and second leaflets 90 and 92 that mimic the three-dimensional anatomical shape of the anterior and posterior leaflets 22 and 24, respectively, of the mitral valve 14. The valve leaflets of the prosthetic valve $12_a$ are joined together at at least two commissural sections 47 that are spaced apart from each other. The prosthetic valve $12_a$ also includes a distal end 86 that defines a first annulus 94 at which the first and second leaflets 90 and 92 terminate.

Additionally, the prosthetic valve $12_a$ includes first and second pairs 102 and 104, respectively, of prosthetic chordae 106 that project from the first and second leaflets 90 and 92 at the first annulus 94. Each of the prosthetic chordae 106 comprises a solid uninterrupted extension of biocompatible material. Each of the first pair 102 of prosthetic chordae 106 has a distal end 108 and each of the second pair 104 of prosthetic chordae has a distal end 110.

As shown in FIG. 11, the second end 44 of the support member 40 may additionally include at least two strut members $45_a$ spaced apart from each other. Each of the at least two commissural sections 47 of the prosthetic valve $12_a$ are attached to a respective one of the strut members 45 to prevent prolapse of the valve leaflets 90 and 92. The strut members $45_a$ are integrally connected to the support member 40 and extend in a generally axial manner along the prosthetic valve $12_a$. The strut members 45a may be attached to the distal ends 108 of the first pair 102 of the prosthetic chordae 106 by sutures, for example. Alternatively, the strut members $45_a$ may be attached to the distal ends 110 of the second pair 104 of the prosthetic chordae 106. It is contemplated that the configuration of the strut members $45_a$ may be varied as needed. For instance, the strut members $45_a$ may have a shorter length than the length of the strut members illustrated in FIG. 11. In this instance, the strut members $45_a$ may be attached at a position proximal to the distal ends 108 and 110 of the prosthetic chordae 106, such as at or near the first annulus 94 of the prosthetic valve $12_a$.

The present invention may be treated with at least one therapeutic agent capable of preventing a variety of pathological conditions including, but not limited to, thrombosis, restenosis and inflammation. Accordingly, the therapeutic agent may include at least one of an anticoagulant, an antioxidant, a fibrinolytic, a steroid, an anti-apoptotic agent, and/or an anti-inflammatory agent.

Optionally or additionally, the therapeutic agent may be capable of treating or preventing other diseases or disease processes such as microbial infections, arrhythmias, and/or heart failure. In these instances, the therapeutic agent may include an antiarrhythmic agent, an inotropic agent, a chronotropic agent, and/or a biological agent such as a cell or protein. More specific types of these therapeutic agents are listed below, including other types of therapeutic agents not discussed above.

Examples of acceptable therapeutic agents include Coumadin, heparin, synthetic heparin analogues (e.g., fondaparinux), G(GP) $II_b/III_a$ inhibitors, vitronectin receptor antagonists, hirudin, antithrombin III, drotrecogin alpha; fibrinolytics such as alteplase, plasmin, lysokinase, factor XIIa, factor VIIa, prourokinase, urokinase, streptokinase; thrombocyte aggregation inhibitors such as ticlopidine, clopidogrel, abciximab, dextrans; corticosteroids such as aldiometasones, amcinonides, augmented betamethasones, beclomethasones, betamethasones, budesonides, cortisones, clobetasol, clocortolones, desonides, desoximetasones, dexamethasones, flucinolones, fluocinonides, flurandrernolides, flunisolides, fluticasones, halcinonides, halobetasol, hydrocortisones, methylprednisolones, mometasones, prednicarbates, prednisones, prednisolones, triamcinolones; fibrinolytic agents such as tissue plasminogen activator, streptokinase, dipyridamole, ticlopidine, clopidine, and abciximab; non-steroidal anti-inflammatory drugs such as salicyclic acid and salicyclic acid derivatives, para-aminophenol derivatives, indole and indene acetic acids (e.g., etodolac, indomethacin, and sulindac), heteroaryl acetic acids (e.g., ketorolac, diclofenac, and tolmetin), arylpropionic acids (e.g., ibuprofen and derivatives thereof), anthranilic acids (e.g., meclofenamates and mefenamic acid), enolic acids (e.g., piroxicam, tenoxicam, phenylbutazone, and oxyphenthatrazone), gold compounds (e.g., auranofin, aurothioglucose, and gold sodium thiomalate), diflunisal, meloxicam, nabumetones, naproxen, oxaprozin, salsalate, celecoxib, rofecoxib; cytostatics such as alkaloids and podophyllum toxins such as vinblastin, vincristin; alkylants such as nitrosoureas and nitrogen lost analogues; cytotoxic antibiotics such as daunorubicin, doxorubicin, and other anthracyclins and related substances, bleomycin, and mitomycin; antimetabolites such as folic acid analogues, purine analogues and related inhibitors (e.g., mercaptopurine, thioguanine, pentostatin, and 2-chlorodeoxyadenosine), pyrimidine analogues (e.g., fluorouracil, floxuridine, and cytarabine), and platinum coordination complexes (e.g., cisplatinum, carboplatinum and oxaliplatinum); tacrolimus, azathioprine, cyclosporine, paclitaxel, docetaxel, sirolimus; amsacrin, irinotecan, imatinib, topotecan, interferon-alpha 2a, interferon-alpha 2b, hydroxycarbamide, miltefosin, pentostatin, porfimer, aldesleukin, bexarotene, and tretinoin; antiandrogens and antiestrogens; antiarrythmics, in particular antiarrhythmics of class I such as antiarrhythmics of the quinidine type (e.g., quinidine, dysopyramide, ajmaline, prajmalium bitartrate, and detajmium bitartrate); antiarrhythmics of the lidocaine type, (e.g., lidocaine, mexiletin, phenyloin, and tocainid); antiarrhythmics of class I C (e.g., propafenone, flecamide (acetate)); antiarrhythmics of class II, including betareceptor blockers such as metoprolol, esmolol, propranolol, metoprolol, atenolol, and oxprenolol; antiarrhythmics of class III such as amiodaron and sotalol; antiarrhythmics of class IV such as diltiazem, and verapamil; and other antiarrhythmics such as adenosine, orciprenaline, and ipratropium bromide.

Other types of therapeutic agents may include digitalis glycosides such as acetyl digoxin/methyldigoxin, digitoxin, and digoxin; heart glycosides such as ouabain and proscillaridin; antihypertensives such as centrally effective anti-adrenergic substances (e.g., methyldopa and imidazoline receptor agonists); calcium channel blockers of the dihydropyridine type, such as nifedipine and nitrendipine; ACE inhibitors (e.g., quinaprilate, cilazapril, moexipril, trandolapril, spirapril, imidapril, and trandolapril); angiotensin-II-antagonists (e.g., candesartancilexetil, valsartan, telmisartan, olmesartan medoxomil, and eprosartan); peripherally effective alpha-receptor blockers such as prazosin, urapidil, doxazosin, bunazosin, terazosin, and indoramin; vasodilators such as dihydralazine, diisopropyl amine dichloroacetate, minoxidil, and nitropiusside-sodium; other antihypertonics such as indapamide, codergocrin mesilate, dihydroergotoxin methane sulphonate, cicletanin, bosentan, and fludrocortisone; phosphodiesterase inhibitors, such as milrinone and enoximone, as well as antihypotonics (e.g., adrenergics and dopaminergic substances such as dobutamine, epinephrine, etilefrine, norfenefrine, norepinephrine, oxilofrine, dopamine, midodrine, pholedrine, and amezinium methyl) and partial adrenoceptor agonists (e.g., dihydroergotamine); fibronectin, polylysines and ethylene vinyl acetates; and adhesive substances such as cyanoacrylates, beryllium, and silica.

Additional therapeutic agents may also include antibiotics and antiinfectives such as R-lactam antibiotics (e.g., β-lactamase-sensitive penicillins, including benzyl penicillins (penicillin G) and phenoxymethylpenicillin (penicillin V)); β-lactamase-resistant penicillins, such as aminopenicillins, which include amoxicillin, ampicillin, and bacampicillin; acylaminopenicillins such as mezlocillin and piperacillin; carboxypenicillines and cephalosporins (e.g., cefazolin, cefuroxim, cefoxitin, cefotiam, cefaclor, cefadroxil, cefalexin, loracarbef, cefixim, cefuroximaxetil, ceftibuten, cefpodoximproxetil, and cefpodoximproxetil); aztreonam, ertapenem, and meropenem; β-lactamase inhibitors such as sulbactam and sultamicillintosilates; tetracyclines such as doxycycline, minocycline, tetracycline, chlorotetracycline, oxytetracycline; aminoglycosides such as gentamicin, neomycin, streptomycin, tobramycin, amikasin, netilmicin, paromomycin, framycetin, and spectinomycin; makrolide antibiotics such as azithromycin, clarithromycin, erythromycin, roxithromycin, spiramycin, and josamycin; lincosamides such as clindamycin and lincomycin; gyrase inhibitors, such as fluoroquinolones, which include ciprofloxacin, ofloxacin, moxifloxacin, norfloxacin, gatifloxacin, enoxacin, fleroxacin, and levofloxacin; quinolones such as pipemidic acid; sulphonamides such as trimethoprim, sulphadiazin, and sulphalene; glycopeptide antibiotics such as vancomycin and teicoplanin; polypeptide antibiotics, such as polymyxins, which include colistin, polymyxin-b, and nitroimidazol derivatives (e.g., metronidazol and timidazol); aminoquinolones such as chloroquin, mefloquin, and hydroxychloroquin; biguanides such as proguanil; quinine alkaloids and diaminopyrimidines such as pyrimethamine; amphenicols such as chloramphenicol; rifabutin, dapsone, fusidinic acid, fosfomycin, nifuratel, telithromycin, fusafungin, fosfomycin, pentamidindiisethionate, rifampicin, taurolidine, atovaquone, and linezolid; virostatics such as aciclovir, ganciclovir, famciclovir, foscamet, inosine (dimepranol-4-acetamidobenzoate), valganciclovir, valaciclovir, cidofovir, and brivudin; tyrosine kinase inhibitors; anti-apoptotic agents such as caspase inhibitors (e.g., fluoromethylketone peptide derivatives), calpain inhibitors, cathepsin inhibitors, nitric oxide synthase inhibitors, flavonoids, vitamin A, vitamin C, vitamin E, vitamin D, pycnogenol, super oxidedismutase, N-acetyl cysteine, selenium, catechins, alpha lipoic acid, melatonin, glutathione, zinc chelators, calcium chelators, and L-arginine; warfarin; betablockers; diuretics; spirolactone; and natural products such as vinca alkaloids (e.g., vinblastine, vincristine and vinorelbine).

As noted above, the therapeutic agent may also include a biological agent. The biological agent may include organic substances such as peptides, proteins, enzymes, carbohydrates (e.g., monosaccharides, oligosaccharides and polysacchardies), lipids, phospholipids, steroids, lipoproteins, glycoproteins, glycolipids, proteoglycans, polynucleotides (e.g., DNA and RNA), antisense polynucleotides (e.g., c-myc antisense), antibodies (e.g., monoclonal or polycolonal) and/or antibody fragments (e.g., anti-CD34 antibody), bioabsorbable polymers (e.g., polylactonic acid), chitosan, extracellular matrix modulators, such as matrix metalloproteinases (MMP), which include MMP-2, MMP-9 and Batimastat; and protease inhibitors.

Biological agents may include, for example, agents capable of stimulating angiogenesis in the myocardium. Such agents may include vascular endothelial growth factor (VEGF), basic fibroblast growth factor (bFGF), non-viral DNA, viral DNA, and endothelial growth factors (e.g., FGF-1, FGF-2, VEGF, TGF). Other growth factors may include erythropoietin and/or various hormones such as corticotropins, gonadotropins, sonlatropin, thyrotrophin, desmopressin, terlipressin, oxytocin, cetrorelix, corticorelin, leuprorelin, triptorelin, gonadorelin, ganirelix, buserelin, nafarelin, and goserelin. Additional growth factors may also include cytokines, epidermal growth factors (EGF), platelet derived growth factor (PDGF), transforming growth factors-R (TGF-R), transforming growth factor-α (TGF-α), insulin-like growth factor-I (IGF-I), insulin-like growth factor-II (IGF-II), interleukin-1 (IL-1), interleukin-2 (IL-2), interleukin-6 (IL-6), interleukin-8 (IL-8), tumour necrosis factor-α (TNF-α), tumour necrosis factor-R (TNF-R), interferon-γ (INF-γ), colony stimulating factors (CSFs); monocyte chemotactic protein, and fibroblast stimulating factor 1.

Still other biological agents may include regulatory peptides such as somatostatin and octreotide; bisphosphonates (e.g., risedronates, pamidronates, ibandronates, zoledronic acid, clodronic acid, etidronic acid, alendronic acid, and tiludronic acid); fluorides such as disodium fluorophosphate and sodium fluoride; calcitonin and dihydrotachystyrene; histamine; fibrin or fibrinogen; endothelin-1; angiotensin II; collagens; bromocriptin; methylsergide; methotrexate; carbontetrachloride and thioacetamide.

The present invention may also be treated (i.e., seeded) with other biological agents, such as cells. Suitable cells may include any one or combination of eukaryotic cells. Additionally or optionally, the cells may be capable of producing therapeutic agents and/or genetically engineered to produce therapeutic agents. Suitable cells for use in the present invention include, for example, progentior cells such as adult stem cells, embryonic stem cells, and umbilical cord blood stem cells. The cells may be autologous or allogenic, genetically engineered or non-engineered, and may include, for example, mesenchymal or mesodermal cells, including, but not limited to, endothelial progenitor cells, endothelial cells, and fibroblasts. Mixtures of such cells can also be used.

A variety of ex vivo or in vivo methods can be used to deliver a nucleic acid molecule or molecules, such as a gene or genes, to the cells. For example, the cells can be modified (i.e., genetically engineered) to produce or secrete any one or combination of the aforementioned therapeutic agents, including, but not limited to, anticoagulant agents, antiplatelet agents, antifibrinolytic agents, angiogenesis factors, and the like. Ex vivo gene transfer is a process by which cells are removed from the body using well known techniques, genetically manipulated, usually through transduction or transfection of a nucleic acid molecule into the cells in vitro, and the returned to the body for therapeutic purposes. This contrasts with in vivo genetic engineering where a gene transfer vector is administered to a patient resulting in genetic transfer into cells and tissues in the intact patient. Ex vivo and in vivo gene transfer techniques are well known to one of skill in the art.

To treat the present invention with at least one therapeutic agent, a variety of methods, agents, and compositions may be used. For example, the therapeutic agent can be simply linked to the stent surface, embedded and released from within polymer materials, such as a polymer matrix, or surrounded by and released through a carrier. Several approaches to treating medical devices with therapeutic agents exist. Some therapeutic agents can be loaded directly onto metallic surfaces; however, a coating composition, typically comprised of at least one polymer and at least one therapeutic agent, is usually used to treat drug-eluting devices. The coating composition ensures retention of the therapeutic agent during deployment and modulates elution kinetics of the therapeutic agent. By altering the release kinetics of different therapeutic agents in the same coating composition, distinct phases of a given disease process may be targeted.

The present invention may be treated with a coating composition comprising at least one therapeutic agent and at least one polymer or oligomer material. The polymer(s) and/or oligomer(s) may be of various types and from various sources, including natural or synthetic polymers, which are biocompatible, biodegradable, bioabsorbable and useful for controlled release of the therapeutic agent. For example, synthetic polymers can include polyesters, such as polylactic acid, polyglycolic acid, and/or combinations thereof, polyanhydrides, polycaprolactones, polyhydroxybutyrate valerates, and other biodegradable polymers or mixtures of copolymers thereof. Natural polymeric materials can include proteins such as collagen, fibrin, elastin, extracellular matrix components, other biologic agents, and/or mixtures thereof.

The polymer material or mixture thereof of the coating composition can be applied with the therapeutic agent on the surface of the present invention and can comprise a single layer. Optionally, multiple layers of the polymer material can be applied to form the coating composition. Multiple layers of the polymer material can also be applied between layers of the therapeutic agent. For example, the polymeric layers may be applied sequentially, with the first layer directly in contact with the uncoated surface of the apparatus and a second layer comprising the therapeutic agent and having one surface in contact with the first layer and the opposite surface in contact with a third layer of polymeric material which is in contact with the surrounding tissue. Additional layers of the polymeric material and therapeutic agent can be added as required.

Alternatively, the coating composition can be applied as multiple layers comprising one or more therapeutic agents surrounded by polymer material. For instance, the coating composition can comprise multiple layers of a single therapeutic agent, one or more therapeutic agents in each layer, and/or differing therapeutic agents in alternating layers. Alternatively, the layers comprising the therapeutic agent can be separated from one another by a layer of polymer material.

The coating composition may further comprise at least one pharmaceutically acceptable polymers and/or pharmaceutically acceptable carriers, for example, non-absorbable polymers, such as ethylene vinyl acetate and methylmethacrylate. The non-absorbable polymer, for example, can aid in further controlling release of the therapeutic agent by increasing the molecular weight of the coating composition and thereby delaying or slowing the rate of release of the therapeutic agent.

The coating composition can be applied to the present invention using standard techniques to cover the entire surface of the apparatus, or partially, as a single layer in a dot matrix pattern, for example. The coating composition can be applied using various techniques available in the art, such as dipping, spraying, vapor deposition, an injection-like and/or a dot matrix-like approach. Upon contact of the coating composition with adjacent tissue where implanted, the coating composition can begin to degrade in a controlled manner. As the coating composition degrades, the therapeutic agent is slowly released into adjacent tissue and the therapeutic agent is eluted so that the therapeutic agent can have its effect locally.

Where the therapeutic agent comprises a biological agent, such as cells, the biological agent can be coated directly onto the surface of the present invention or, alternatively, they can be incorporated into the polymeric material (e.g., into a polymer matrix). Such biological agents may also be included within at least one microscopic containment vehicle (e.g., a liposome, nanocapsule, nanoparticle, micelle, synthetic phospholipid, gas-dispersion, emulsion, microemulsion, nanosphere, and the like) that can be stimulated to release the biological agent(s) and/or that release the biological agent(s) in a controlled manner. The microscopic containment vehicle can be coated onto the surface of the present invention or incorporated into the polymeric material. Where the biological agent comprises cells, for example, the cells can be induced to produce, activate, and/or release their cellular products (including one or more therapeutic agents) by an external stimulation device (e.g., an electrical impulse). Alternatively, cells can constitutively release one or more therapeutic agents at a desired level.

To enable delivery and deployment of the apparatus 10, the apparatus is positioned about a balloon 120 (FIG. 1) for expanding the main body portion 46 of the support member 40 into full and complete contact with the annulus 20 of the mitral valve 14. The balloon 120 may have an hourglass shape to conform to the concave cross-sectional configuration of the main body portion 46. The shape of the balloon 120 is defined by first and second bulb sections 122 and 124 connected by a center section 126. Each of these sections 122, 124 and 126 may have a D-shaped diameter (or other shaped diameter) to match the D-shaped diameter of the valve 14 and the prosthetic valve 12. The center section 126 of the balloon 120 has a smaller diameter than the bulb sections 122 and 124. The first and second bulb sections 122 and 124 and the center section 126 may be inflated together or separately. Further, the sections 122, 124 and 126 may have multiple chambers to accommodate multiple fluids (i.e., an inflation fluid and a cooling fluid).

In addition, releasable constraining wires (not shown) are used to temporarily hold the upper wing members 60 and the lower wing members 70 in the radially collapsed conditions shown in FIG. 1 during delivery and placement of the apparatus 10. The constraining wires can be made from a variety of different materials including metals, polymers, synthetics, fabrics, and biological tissues. With the upper wing members 60, the lower wing members 70, and the main body portion 46 of the support member 40 in their collapied conditions, the apparatus 10 is then loaded into the end of a 16 to 22 French catheter 128 in a known manner.

To replace the mitral valve 14 with the apparatus 10 using a percutaneous (or intravascular) approach, the apparatus is first sized for the particular mitral valve using fluoroscopic and/or echocardiographic data. The catheter 128 is then introduced into either the right or left jugular vein (not shown), a femoral vein (not shown), or the subclavian vein (not shown) using a known percutaneous technique, such as the Seldinger technique, and is advanced through the superior or inferior vena cava (not shown) to approach the right atrium (not shown). The catheter 128 is passed through the interatrial septum (not shown) to reach the left atrium 16. From inside the left atrium 16, the apparatus 10 is then positioned within the annulus 20 of the mitral valve 14 as is shown in FIG. 1. It should be noted that the angular orientation of the apparatus 10 within the mitral valve 14 is important, so a diagnostic agent or agents, such as radiopaque markers (not shown), may be used to ensure the apparatus is rotated to the proper position prior to deployment.

Next, the catheter 128 is pulled back so that the support member 40 can expand to the condition shown in FIG. 2 in the annulus 20 of the native mitral valve 14. The balloon 120 is then inflated, which pushes the main body portion 46 of the support member 40 into engagement with the annulus 20 as shown in FIG. 5.

Figure 5:
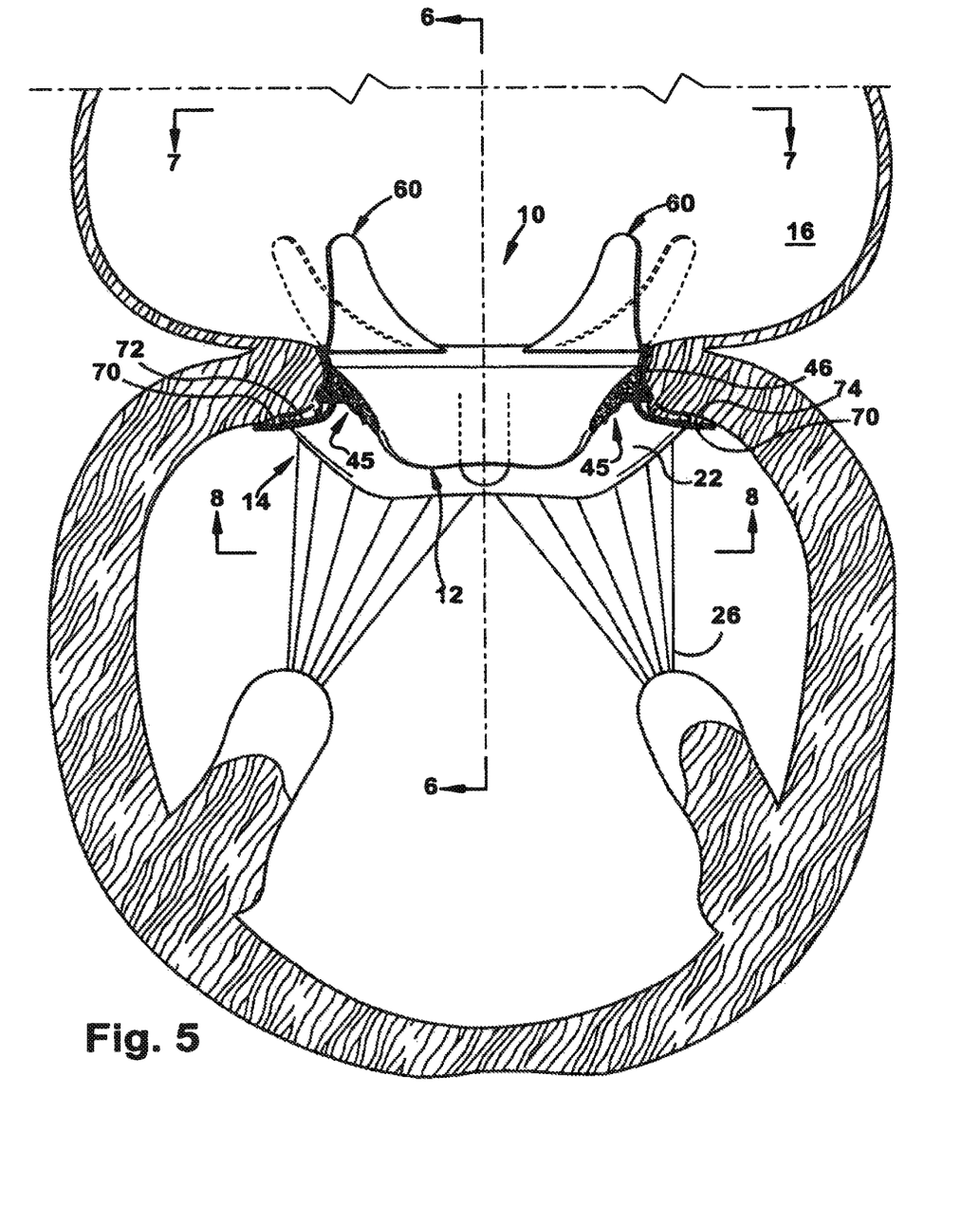
FIG. 5 is a view similar to FIG. 1 illustrating the placement of the apparatus in the annulus of the cardiac valve in the expanded condition.

The constraining wires are then released, which allows the upper wing members 60 and the lower wing members 70 of the support member 40 to spring radially outward toward their expanded conditions illustrated in FIGS. 2-8. The upper wing members 60, in their radially extended condition, extend transverse to the direction of blood flow through the prosthetic valve 12, and engage the wall of the left atrium 16. Where the attachment mechanism 62 comprises barbs 64 as shown in FIG. 5, the barbs embed into the wall of the left atrium 16 to help secure the support member 40 in the annulus 20 of the mitral valve 14.

As the lower wing members 70 move from their radially collapsed condition to their radially extended condition, each of the lower wing members engages a portion of the native valve leaflets 22 and 24. The first and second lower wing members 72 and 74 engage the commissures of the native mitral valve 14 (FIG. 5), while the third and fourth lower wing members 76 and 78 engage respective central portions of the native valve leaflets 22 and 24 (FIG. 6). The barbs 64 on the lower wing members 70 embed into the native valve leaflets 22 and 24 to help secure the support member 40 in the annulus 20 of the mitral valve 14. In their radially extended condition, the lower wing members 70 pin the native leaflets 22 and 24 back against the valve annulus 20 so that the prosthetic valve 12 can assume the valvular function. With the apparatus 10 fully deployed, the balloon 120 is deflated and moved out of the valve annulus 20.

It should be noted that the engagement of the main body portion body 46 with the valve annulus 20, the engagement of the upper wing members 60 with the wall of the left atrium 16, and the engagement of the lower wing members 70 that pins the native valve leaflets 22 and 24 back against the valve annulus provides a unique three-way locking mechanism for securing the apparatus 10 in the valve annulus.

It is contemplated that the apparatus 10 according to the present invention could alternatively be placed by a retrograde, percutaneous approach. For example, the apparatus 10 may be urged in a retrograde fashion through a femoral artery (not shown), across the aortic arch (not shown), through the aortic valve (not shown), and into the left ventricle 18 where the apparatus may then be appropriate positioned in the native mitral valve 14.

Figure 12:
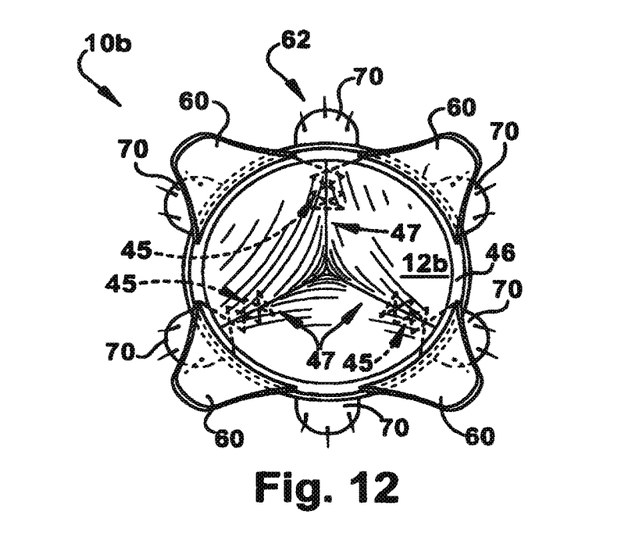
FIG. 12 is a schematic top view similar to FIG. 7 and illustrating an alternate embodiment of the apparatus.

FIG. 12 illustrates another alternative embodiment of the present invention. The apparatus 10$_b$ of FIG. 12 is identically constructed as the apparatus 10 of FIGS. 2-8, except whereas described below. In FIG. 12, structures that are identical as structures in FIGS. 2-8 use the same reference numbers, whereas structures that are similar but not identical carry the suffix "b".

As shown in FIG. 12, the apparatus 10$_b$ comprises a tri-leaflet prosthetic valve 12$_b$. Examples of tri-leaflet prosthetic valves, such as the prosthetic valves disclosed in U.S. Pat. No. 5,156,621, which is hereby incorporated by reference in its entirety, are known in the art. The tri-leaflet prosthetic valve 12$_b$, such as a porcine aortic valve, may be used in either the mitral or tricuspid position. The prosthetic valve 12$_b$ may be made of other biological materials, including, but not limited to, aortic xenografts, bovine pericardial tissue, equine pericardial tissue, porcine pericardial tissue, peritoneal tissue, and a homograft or allograft. Additionally, the prosthetic valve 12$_b$ may be made of any one or combination of biocompatible materials such as polyurethane, PTFE, expanded PTFE, Dacron®, woven velour, Gore-Tex®, and heparin coated fabric.

As may be seen in FIG. 12, in the tricuspid position, six lower wing members 70 may be used so that a lower wing member is positioned at each native commissure and directly over each native valve leaflet. The support structure 40 of the apparatus 10$_b$ also includes at least three strut members 45 that are spaced apart from each other. The valve leaflets of the prosthetic valve 12$_b$ are joined together at at least three commissural sections 47. Each of the three commissural sections 47 are attached to a representative one of the strut members 45 to prevent prolapse of the valve leaflets 22 and 24. Other than this, the apparatus 10$_b$ with the tri-leaflet prosthetic valve 12$_b$ is deployed and functions as described above with regard to the previous embodiment. It should be understood that more or less than six lower wing members 70 could be used.

The present invention thus allows for the apparatus 10 to be delivered in a cardiac catheterization laboratory with a percutaneou approach under local anesthesia using fluoroscopic as well as echocardiographic guidance, thereby avoiding general anesthesia and highly invasive open heart surgery techniques. This approach offers tremendous advantages for high risk patients with severe valvular disease. It should be understood, however, that the present invention contemplates various other approaches, including standard open heart surgeries as well as minimally invasive surgical techniques. Because the present invention omits stitching of the apparatus 10 in the valve annulus 20, surgical time is reduced regardless of whether an open, minimally invasive or percutaneous approach is used.

From the above description of the invention, those skilled in the art will perceive improvements, changes and modifications. For example, it should be understood by those skilled in the art that the various portions of the support member 40 could be self-expanding or expanded by a change in temperature (because they are made from a shape memory material). Such improvements, changes and modifications within the skill of the art are intended to be covered by the appended claims.

Having described the invention, we claim:

1. A method for replacing a native cardiac valve having at least two native valve leaflets, said method comprising:
providing a prosthetic valve that includes an expandable support member having oppositely disposed first and second ends and a main body portion extending between the first and the second ends, and having a biocompatible material covering an entire circumference of an inside surface thereof, a plurality of upper wing members that extend integrally from the first end of the support member and are spaced about the circumference of the main body portion, and a plurality of lower wing members that extend integrally from the second end of the support member, wherein the expandable support member further comprises at least two strut members spaced apart from each other and physically attached to the prosthetic valve along at least two commissural sections;
temporarily holding the upper wing members and the lower wing members in a radially collapsed configuration during surgery;

expanding the expandable support member to physically engage a circumferential region of the support member with an annulus of the native cardiac valve to exert sufficient force to pin the native leaflets against the annulus of the cardiac valve;

releasing a plurality of constraining wires to allow the upper and the lower wing members to expand radially outward to an expanded configuration, wherein the upper wing members are transverse to the direction of blood flow; and securing the prosthetic valve in the annulus of the native cardiac valve such that the upper wing members expand to physically contact a first section of cardiac tissue spaced away from the native leaflets and surrounding the annulus of the native cardiac valve.

2. The method of claim 1, wherein (1) engagement of the circumferential region of the support member with the leaflets of the native cardiac valve, (2) engagement of the upper wing members with the first section of cardiac tissue spaced away from the native leaflets and (3) engagement of the lower wing members with the native valve annulus establishes an integral three-way locking mechanism securing the prosthetic valve to the first section of cardiac tissue and to the annulus of the native cardiac valve.

3. The method of claim 1, wherein deployment of a separate attachment mechanism from the upper wing members-embeds the separate attachment mechanism into the first section of cardiac tissue spaced away from the native leaflets.

4. The method of claim 3, wherein the separate attachment mechanism includes at least one barb and said method comprises embedding the at least one barb into the first section of cardiac tissue.

5. The method of claim 1, wherein a step of actuating the plurality of constraining wires moves the upper wing members into direct contact with a wall of the left atrium.

6. The method of claim 1, wherein the step of releasing the constraining wires positions each of the upper wing members radially outward to engage the first section of cardiac tissue spaced away from the native leaflets and positions the lower wing members to engage the native valve annulus.

7. The method of claim 6, wherein the first section of cardiac tissue is a wall of the left atrium.

8. The method of claim 1, wherein a step of inserting the prosthetic valve into the annulus of the native cardiac valve is done via a jugular vein.

9. The method of claim 1, wherein at least a portion of the expandable support member is treated with a therapeutic agent for eluting into cardiac tissue proximate to the expandable support member.

10. The method of claim 1, wherein the prosthetic valve is comprised of at least one suture attachment mechanism and the method further comprises releasing a suture connected to the suture attachment mechanism.

11. The method of claim 1, wherein a tissue portion of the prosthetic valve is constructed of a single piece of pericardial tissue.

12. The method of claim 1, wherein a tissue component of the prosthetic valve is treated with a dry tissue valve procedure and an anti-calcification solution.

* * * * *